United States Patent [19]

Barkett et al.

[11] Patent Number: 4,709,331
[45] Date of Patent: Nov. 24, 1987

[54] CALCULATOR-COMPUTER FOR CALCULATING INFUSION RATES OVER VARYING TIME INTERVALS

[76] Inventors: Patricia A. Barkett, 5420 SW. 163rd Ave., Fort Lauderdale, Fla. 33331; Michael G. Clapp, 5678 NW. 195th Terr., Opa-Locka, Fla. 33055

[21] Appl. No.: 605,808

[22] Filed: May 1, 1984

[51] Int. Cl.$^4$ .............................................. G06F 15/42
[52] U.S. Cl. .................................... 364/413; 364/706; 364/716
[58] Field of Search ............... 364/413, 706, 709, 715, 364/716, 710, 414, 415

[56] References Cited

U.S. PATENT DOCUMENTS

| Re. 30,671 | 7/1981 | Poland | 364/706 |
|---|---|---|---|
| T101,701 | 4/1982 | Egbert | 364/706 |
| 4,001,569 | 1/1977 | Dickinson et al. | 364/716 X |
| 4,048,474 | 9/1977 | Olesen | 364/413 |
| 4,092,523 | 5/1982 | Taug et al. | 364/408 X |
| 4,100,401 | 7/1978 | Tutt et al. | 364/705 X |
| 4,128,889 | 12/1978 | Ojima et al. | 364/705 |
| 4,228,516 | 10/1980 | Johnston, Sr. | 364/710 X |
| 4,282,514 | 8/1981 | Elkin et al. | 235/310 |
| 4,308,866 | 1/1982 | Jeliffe et al. | 364/413 X |
| 4,321,461 | 3/1982 | Walter, Jr. et al. | 377/21 |
| 4,379,640 | 4/1983 | Inoue | 364/710 X |
| 4,405,991 | 9/1983 | Stanley et al. | 219/10.55 |
| 4,458,320 | 7/1980 | Sutton | 364/709 X |
| 4,625,292 | 11/1986 | Philp | 364/569 |

FOREIGN PATENT DOCUMENTS 254525 10/1984 France ................... 364/413

Primary Examiner—Jerry Smith
Assistant Examiner—Charles B. Meyer
Attorney, Agent, or Firm—Frank L. Abbott

[57] ABSTRACT

A calculator, particularly useful for medical personnel comprises function, numerical selection, and memory circuits with a read out display connected to provide conversion of quantitative values from one system to another, times and converts pulse rates and similar observations to a standard time element, and when used with a data, time, tone and circuitry reminds an attendant of various duty schedules and is also adapted to be utilized with a "print out" system.

6 Claims, 5 Drawing Figures

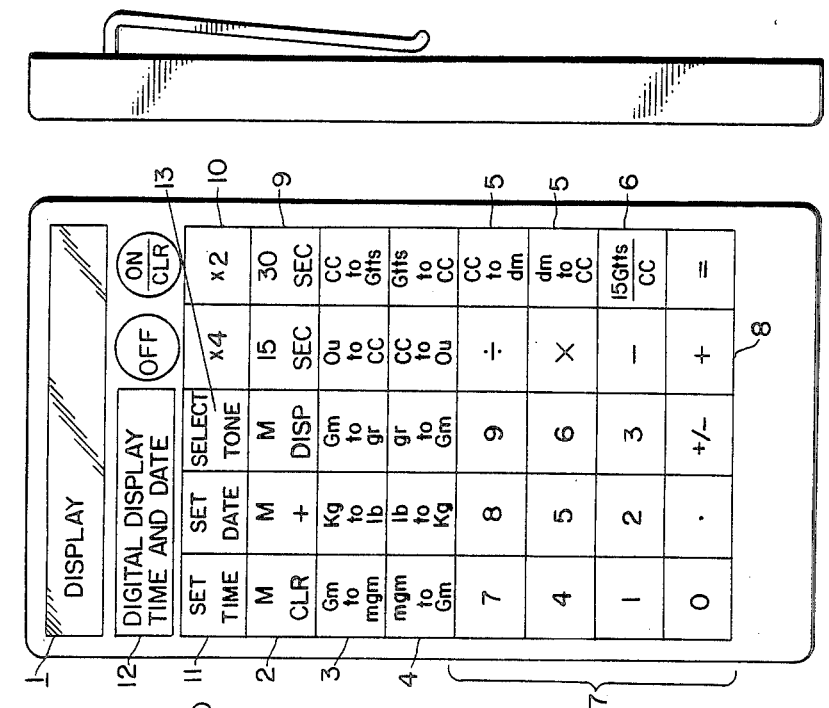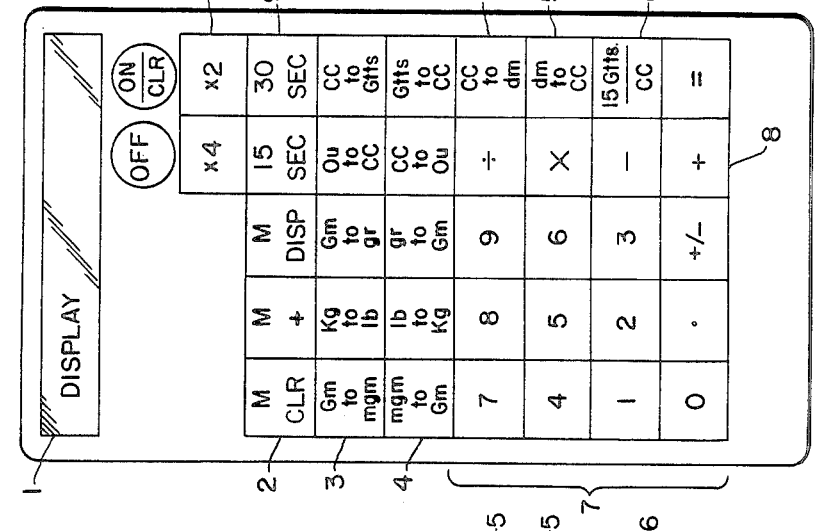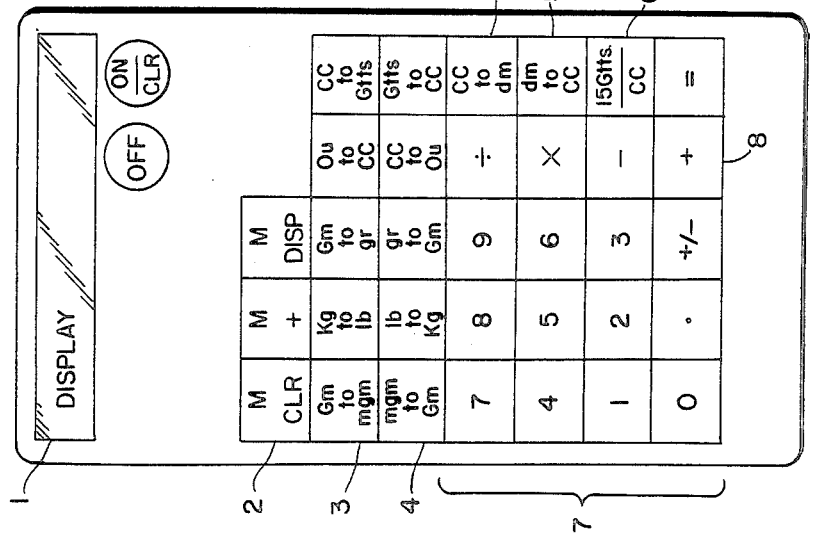

CALCULATOR-COMPUTER FOR CALCULATING INFUSION RATES OVER VARYING TIME INTERVALS

BACKGROUND OF THE INVENTION

Heretofore technicians and professionals in many fields have been forced to rely upon memory for converting from one measurement system to another and their knowledge of various mathematical processes. In the medical profession it has been necessary to convert dosages from one measurement system to another, to determine pulse rates for a standard unit of time, etc. The present invention eliminates guess work by use of a small computer-calculator which places in the hands of the medical profession an on the spot means for providing accurate information through conversion programs and specifically medically oriented function and numerical value selection circuits.

The prior art devices disclose calculators adapted to various specific uses but none that can provide the variety of information of the instant invention or specifically adapt to information useful to the medical profession.

Examples of prior art devices are disclosed in U.S. Pat. No. 4,100,602 which converts a quantitative item in a recipe to the fraction required based on the servings desired relative to servings provided for by the recipt. To obtain the desired information on the display requires six entries for the first item and four entries for each additional item. No medical application is apparently anticipated.

U.S. Pat. No. 4,101,071 discloses a calculator to determine the rate of timing total calories burned in relation to the pulse rate. It does not relate to the present invention and is limited to giving the burn rate or total calories burned.

U.S. Pat. No. 4,228,516 is related to a system for converting English to metric units and vice versa with an input and output display. It appears not to recognize the problem solved by the device of this application and it appears largely concerned with the device for selecting conversion factors.

U.S. Pat. No. 4,290,113 is concerned with a minicomputer for conversion from common units into SI units in response to factor selection based upon a letter code for types of material commonly used in medicine and related fields. The minicomputer is also capable of performing conventional mathematical functions.

As will be seen from the subsequent description of the invention the prior art does not disclose the function or the structure essential to the invention herein disclosed and claimed.

SUMMARY OF THE INVENTION

There is provided, according to the instant invention a computer or calculator which may be carried in the hand or attached to the user's uniform or other clothing and especially adapted for use by the medical profession.

It is comprised of an entry keyboard for numbers, function keys which are programmed to convert a selected quantitative unit to another unit. It also has a display register indicating the converted value, a memory register which when used the results appear on the display register. In some modifications there are time and date reminder circuits with a display register and a tone signal to remind the user of a schedule time and date for performance of a duty. In addition there are provisions for timed numerical conversions.

One object of the invention is to provide a quick, accurate means for calculating and converting dosages in one system of measurement to another system, thereby eliminating the mistakes which may occur from a faulty memory or errors in mathematics and at the same time providing in a minimum of time an accurate on the spot result.

Another object is to provide special function keys which for example, convert fifteen drops to cubic centimeters. This function is particularly important in intravenous fluid administration to calculate the IV drip rate. The IV drip rate must be accurately and quickly determined to avoid complications.

A further object of the invention is to provide a time signal and specific time interval values for determining a sixty second pulse rate. This is provided by 15 and 30 second keys which when used with the numeral and either the 2 or 4 multiple keys give the pulse rate per minute.

Another object of the invention is to provide a date and time program with read out on a date time register. It is imperative in medical practice that a strict schedule of treatment and medicines be maintained, and that records reflect the time and date of entries therein. It is also an object of the invention to provide a tone signal which will remind an attendant of the elapse of a specific time interval or the awareness of a schedule to be maintained.

Another object of the invention is to provide a calculator or computer also capable of performing basic mathematical functions.

Other objects and advantages of the instant invention will become readily apparent to those skilled in the art from reading of the following detailed description of the invention related to the drawings and appended claims. It will also be apparent to those skilled in the art that this invention is not limited to use in the medical profession but has broad application in other arts where time saving conversions, accurate determinations and time and rate determinations are material.

BRIEF DESCRIPTION OF THE DRAWINGS

FIG. 1 is a view of one embodiment of the calculator-computer.

FIG. 2 is a view of the invention involving a pulse rate timing and determining means.

FIG. 3 illustrates an embodiment which, in addition to the details of the other embodiments, includes a time, date and tone.

FIG. 4 illustrates a side view of the calculator clearly showing the clip for attaching it to a supporting person or element.

DETAILED DESCRIPTION

Figure 5:
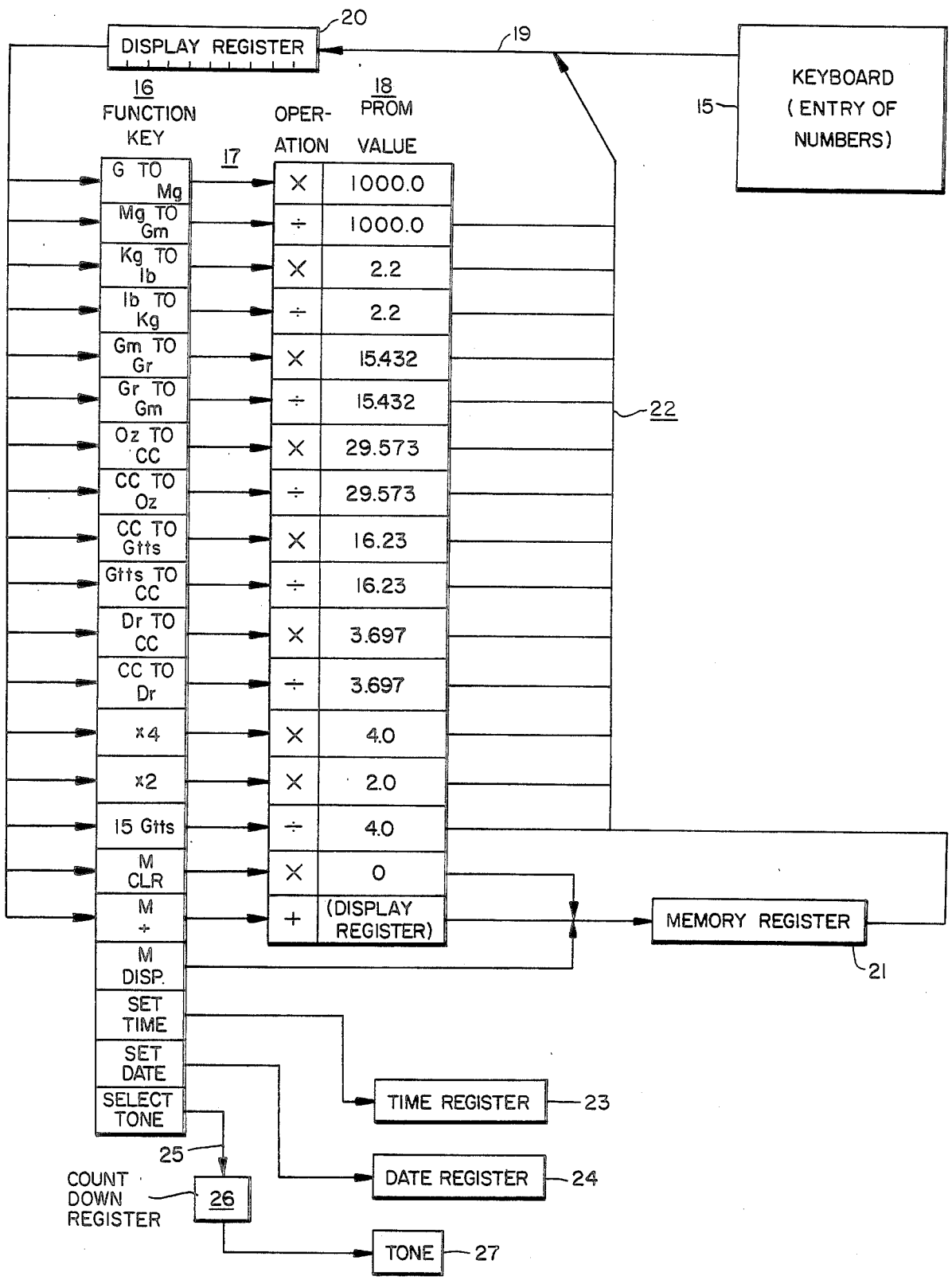
FIG. 5 illustrates a schematic circuit diagram exemplary of the circuitry for the invention.

In reference to the figures of the drawing, it is pointed out that a calculator-computer is disclosed which has conventional pocket calculator elements such as a power supply (not shown), an off switch and an on/-clear switch.

In FIGS. 1, 2 and 3 there are illustrated keyboards for the computer which includes a display register 1 wherein on demand digital answers and information stored in the memory register appear.

Each of the keyboards has memory circuit keys indicated generally at 2 and comprised of memory clear, MCLR; memory add, M+; and memory display, MDISP keys.

Each keyboard has conversion function keys, those in row 3 comprised of conversion of Gm to Mgm; grams to milligrams; Kg to Lb; kilograms to pounds; Gms to gr; grams to grains; Oz to cc; ounces to cubic centimeters; and cc to gtts, cubic centimeters to drops. In each instance the function keys in row 3 convert larger units of measure to smaller units by multiplying the larger units by a constant programmed into the calculator. The function keys in row 4 perform the converse or opposite function namely conversion of a smaller unit to a larger unit by dividing the smaller unit by a constant programmed into the circuit. There are also keys 5, one of which functions to convert cubic centimeters to drams and the other to convert drams to cubic centimeters.

Function key 6 converts 15 drops (gtts) to cubic centimeters.

The keys 7 are the numerical value keys, zero through nine, and the keys indicated generally at 8 are mathematical function keys which permit the use of the calculator-computer as a conventional hand held calculator.

Frequently in medical practice the attendants are called upon to compute dosages, this involves converting from one measurement unit or system to another, which requires the attendant to rely upon memory for the equivalency factors for conversion as well as requiring mental or written mathematical computations. Obviously, such a procedure has built in propensities for error. For example, the attendant may rely upon the wrong factor or make arithmetic errors. It is believed that the error rate increases with increased time pressures produced by increases in the number of patients per attendant.

With the present invention, for conversion from one unit to another, the attendant selects the numeric value by pressing the appropriate key or keys 7 and then the function key for conversion. For example, to convert 5 grams to milligrams, key 7, numbered 5, would be pressed and key 4 labeled Gms to Mg would be pressed which would activate the program to multiply the numeral 5 by the programmed value 1,000 and the answer, 5,000 Mgs would be immediately read on the Display Register. As shown in FIG. 5 the numeric values go into the display register and into the programmed function circuit which when the function switch is activated displays the answer.

The use of a calculator-computer obviously increases accuracy and reduces the time spent in calculating and administering medical services.

A special application is performed by function key 6, 15 gtts (drops or minims) which provides accuracy in determining intravenous infusion rates of drops per minute. In intravenous administration the drip rate is critical. Therefore, for example, given an administration set which gives the standard 15 gtts (drops) per cc (cubic centimeter) and a 1,000 cc IV bag to infuse over a 10 hour period, the user can determine the exact number of drops to infuse per minute by completing a simple two step process. The bag size of 1,000 cc's is entered by pressing key 1 once and key 0 three times. This amount to be infused is then divided by the number of hours the bag is to run, 10. The user presses the ÷, division key 8 followed by pressing key 1 once then key 0. The answer 100 (cc's per hour) will appear on the display register. The user now presses special function key 6 which gives the number of drops per minute required to maintain an accurate infusion rate. The answer of 25 (gtts) per minute) will appear on the display register.

15 gtts per cc has been adopted because it is frequently used dosage standard, however, the disclosed calculator-computer may be programmed for other dosages utilizing other measures. For example, 10 gtts per cc could be introduced in the program in addition to or instead of 15 gtts.

For foregoing structure and functions are features of each of the exemplary embodiments of the invention.

Referring now to FIG. 2, in addition to the previously described programs, functions and value circuits, FIGS. 2 and 3 have therein a pulse rate computer function circuit. This is selected and controlled by multiple keys 10, x4 and x2 and time interval keys 9, 15 sec and 30 sec.

It also has a tone signal to sound when a selected time interval has elapsed. A medical attendant desiring to read a pulse rate sets the desired time interval, for illustrative purposes the time interval has been selected as either 15 or 30 seconds, when the selected interval has elapsed the time tone signal will sound, the pulse for the interval will be entered by pressing the appropriate numeric value switch or switches and one of the keys 10 will be pressed which is appropriate to the time interval selected, the pulse rate per minute then appears on the display. This system of pulse rate determination provides an accurate, quick means which eliminates the chances of mathematical error and errors caused by various distractions which often occur in usual practices.

The calculator-computer illustrated in FIG. 3 includes all of the features of the embodiments of FIGS. 1 and 2, in addition has time and date select keys 11 and a digital time and date display 12 as well as tone select key 13. Medical personnel working in a hospital or clinic must have means for providing date and time. This is necessary to provide accurate date and time in the medical record and for date and time management of scheduled medications and treatments. The keys 11 set the correct time and date on the digital display whereby the calculator-computer functions as a conventional calendar clock. The tone select key 13 permits the operator to obtain an audible signal on the hour, half hour or quarter hour to remind him/her that certain functions must be performed, such as checking vital signs, administering medications or therapy, etc.

Since a hospital is normally a busy place and frequently understaffed, it becomes necessary that any means that will save time and free the hands of the professionals is a decided benefit, therefore, on the back of the calculator-computer is a clip 14 which will be used to attach the calculator-computer to the clothing of the attendant or to a convenient supporting surface such as a clip board.

In FIG. 5 a schematic view of the circuitry involved is presented. It is comprised of numeric keyboard 15 and a functions keyboard 16, the functions keyboard is connected through circuits to the program data indicated generally by 18. The numeric keyboard 15 is connected through circuit 19 to the display register 20 and memory register 21, whereby when the appropriate function key in 16 has been pressed and the numeral key in 15 has been pressed the answer appears on the display register 20 or if the memory key in row 2 has been pressed, the answer is placed in the memory register to be displayed in the display 1. Besides the programmed data, connected into circuit 22 is a time register 23 and a date register 24 which are connected by appropriate circuitry to a display 12. In conjunction with the previously disclosed circuitry are time and date set keys 11 which act with the respective registers 23 and 24 to provide a digital time and date on the display 12. The signal tone circuit 25 is activated by count down set and timing circuit to transmit a signal to a count down register which activates a tone generator when a programmed interval of time has elapsed.

Obviously the circuits illustrated in FIG. 5 are directed to the most complicated modification of the calculator-computer and the circuits for other modification are similar but do not contain elements which are not necessary to the conversions and uses of the specific embodiment.

Disclosed herein are modifications of the calculator-computer which is of particular application to the medical profession. For clarity, conversions from one measurement system to another and in the functions involving time specific time intervals have been setforth by way of example; it is within the scope of this invention to utilize the disclosed calculator-computer with conversions for different systems of measurement and for different time intervals.

Specific embodiment of a hand held calculator-computer have been described, the embodiments enable an operator to eliminate many opportunities for error, shorten the time and improve the accuracy of determinations regularly and frequently performed by medical attendants. There is also provided a timing circuit which will limit the chances for inaccuracy or errors in the time when the functions are performed. In addition to the specialized uses, the instrument may be used as a calculator and a digital clock providing time and date.

It is also pointed out that operation of the disclosed calculator-computer involves very few manual movements, thereby limiting the chances for error.

Since various modifications within the spirit of the invention may occur to those skilled in the art, it is intended that no limitation be placed on the invention except as defined by the scope of the appended claims.

We claim:

1. A calculator-computer comprised of conventional numerical keys, function keys, an on and clear switch, an off switch, a power source and display and memory registers in combination with program means for converting from one system of measurement used by the medical profession to another and for determining certain infusion rates in a standard measurement system for a selected time period, conversion keys and circuit means connecting said conversion keys and said numerical and function keys to activate and obtain results from said program means in a minimum number of manual steps and to display said results directly on said display register without the display of intermediate determinants, additional circuitry connecting time interval keys to a timing device for selecting predetermined time intervals and circuitry connecting the time interval keys with said conversion keys for activating means to convert a number of events in the time interval previously selected to the number of events which at the same rate of occurrence would occur in a shorter or longer interval.

2. The combination defined in claim 1 in which said time interval keys indicate time intervals of 15 seconds and 30 seconds and said conversion keys represent x4 and x2, whereby when a medical professional has determined a pulse rate for a selected portion of a minute, 15 or 30 seconds, entry of the rate and converting x4 or x2 by pressing the appropriate conversion key automatically displays the pulse rate per minute or other time interval.

3. The combination of claim 1 including digital time and date registers, a tone generator, connected to a time and date display register and circuitry connecting said time register to a time set key, said date register to a date set key and circuitry means to provide a date and/or time on the time and date display when said keys close said circuit, said tone generator being connected through a count down register to a tone select key which closes said circuit to cause a tone to sound when a preselected time interval has elapsed.

4. The combination of claim 1 combined with a clip mounted on the back of the calculator-computer, said clip being downwardly open so that it may grasp a portion of a user's clothing or another supporting surface thereby freeing the hands of the user.

5. A calculator-computer comprised of a keyboard having numerical value keys, zero through nine; mathematical function keys for performing addition, substraction, multiplication and division; also equal and decimal keys; an on and clear switch; a power source; an off switch and display and memory registers combined with a conversion program, keys controlling access to the program to convert grams to milligrams, kilograms to pounds, grams to grains, ounces to cubic centimeters, cubic centimeters to drops, milligrams to grams, pounds to kilograms, grains to grams, cubic centimeters to ounces, drops to cubic centimeters, cubic centimeters to drams, drams to cubic centimeters and fifteen drops to cubic centimeters, circuit means connecting said keys and display whereby using said keys causes activation of the selected circuit to produce the sought after result directly on the display register without the display of intermediate determinants, and means whereby an infusion rate may be determined by entering a rate for one volume of fluid per a selected time element said means will directly produce on the display register the rate of a different volume of fluid for a different preselected time element, time interval keys indicating time intervals of 15 seconds and 30 seconds, a timing device, and circuitry connecting said time interval keys to said timing device and other conversion keys, x4 and x2, representing multiplication by four and by two respectively circuitry connecting said other conversion keys with said numerical value keys to convert a numerical value entered to a value that equals two or four times said numerical value whereby when a medical professional has determined a pulse rate for a selected portion of a minute, 15 or 30 seconds, entry of the rate and x4 or x2 key automatically displays the pulse rate per minute.

6. The combination of claim 5 which includes a digital time register, a date register, connected to a digital time and date display, a time set key and a date set key, where said time set key and said date set key are each connected by circuit means to the time and date display, such that time is displayed when the said time set key is depressed to close said time and date displaying circuit means and such that the date is displayed when the date set key is depressed to close said time and date displaying circuit means, where said time and said date may be displayed simultaneously or individually, a count down register, a tone generator and a select tone key, a circuit means connecting said select tone key through said count down register to said tone generator whereby when a selected time interval has elapsed, a tone signal is produced.

* * * * *